US00PP29540P2

(12) United States Plant Patent
Smith

(10) Patent No.: US PP29,540 P2
(45) Date of Patent: Jul. 24, 2018

(54) ***CHRYSANTHEMUM* PLANT NAMED 'CIFZ0051'**

(50) Latin Name: *Chrysanthemum x morifolium*
Varietal Denomination: CIFZ0051

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/530,504

(22) Filed: Jan. 23, 2017

(51) Int. Cl.
*A01H 5/02* (2018.01)

(52) U.S. Cl.
USPC ..... Plt./292

(58) Field of Classification Search
USPC ..... Plt./292
See application file for complete search history.

*Primary Examiner* — Annette H Para
(74) *Attorney, Agent, or Firm* — Dale Skalla

(57) ABSTRACT

A new garden type *Chrysanthemum* plant named 'CIFZ0051' particularly distinguished by the medium size plant with round mound plant habit, a medium-small size pink/lavender flower color and a natural season response in early-mid October.

1 Drawing Sheet

Latin name of the genus and species of the plant claimed: *Chrysanthemum x morifolium.*

Varietal denomination: 'CIFZ0051'.

BACKGROUND OF THE NEW PLANT

The present invention comprises a new *Chrysanthemum*, botanically known as *Chrysanthemum x morifolium*, and hereinafter referred to by the variety name 'CIFZ0051'.

'CIFZ0051' is a product of a planned breeding program. The new cultivar has medium size plant with round mound plant habit, a medium-small size pink/lavender flower color and a natural season response in early-mid October.

'CIFZ0051' originated from a mutation: Female parent x-rayed at 1750 RAD in October of 2013. Single cutting sport from the female parent.

The female parent was an unnamed pink/lavender seedling from own breeding '10-M078'.

TABLE 1

| When compared to the female parent, 'CIFZ0051' has: |
|---|
| (1) Similar flower type and size but darker lavender/pink color than the sport parent |
| (2) Blackcloth is similar and natural season respone is similar or a day or two faster than the sport parent |
| (3) Similar plant habit and overal plant size than the sport parent |

No male parent.

The first act of asexual reproduction of 'CIFZ0051' was accomplished when vegetative cuttings were propagated from the initial selection, this initial selection took place on Apr. 16, 2014 in Gilroy, Calif.

BRIEF SUMMARY OF INVENTION

Horticultural examination of plants grown from cuttings of the plant initiated in May 2014 in Gilroy, Calif., and continuing thereafter, has demonstrated that the combination of characteristics as herein disclosed for 'CIFZ0051' are firmly fixed and are retained through successive generations of asexual reproduction.

'CIFZ0051' has not been observed under all possible environmental conditions. The phenotype may vary significantly with variations in environment such as temperature, light intensity and day length.

'CIFZ0051' has not been made publicly available prior to the effective filing date of this application, notwithstanding any disclosure that may have been made less than one year prior to the effective filing date of this application by the inventor or another who obtained 'CIFZ0051' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0051' with colors being as true as possible with an illustration of this type. The photographic drawings show in FIG. 1 a close view of flower of the new variety and in FIG. 2 a flowering plant from an outdoor trial.

Figure 1:
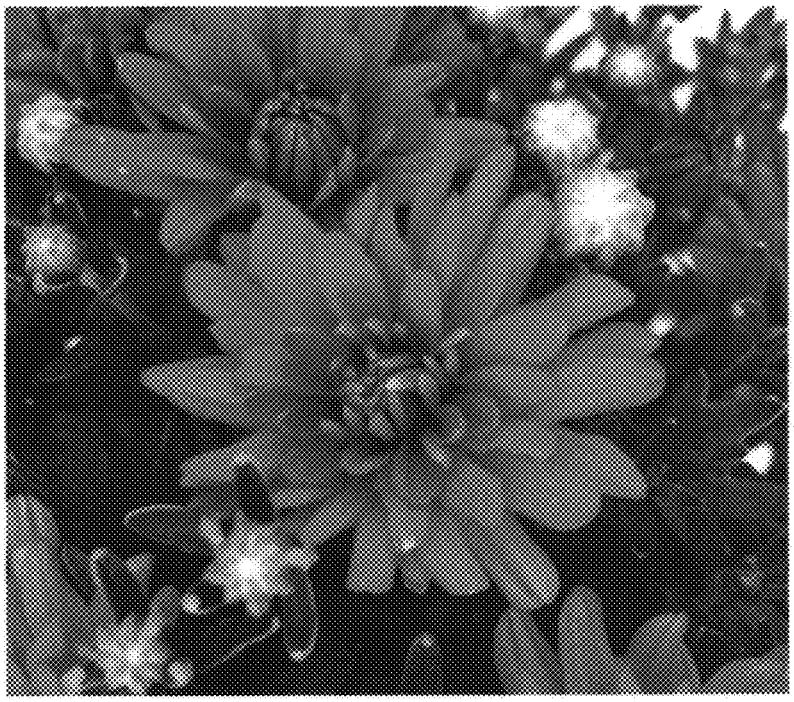
Figure 2:
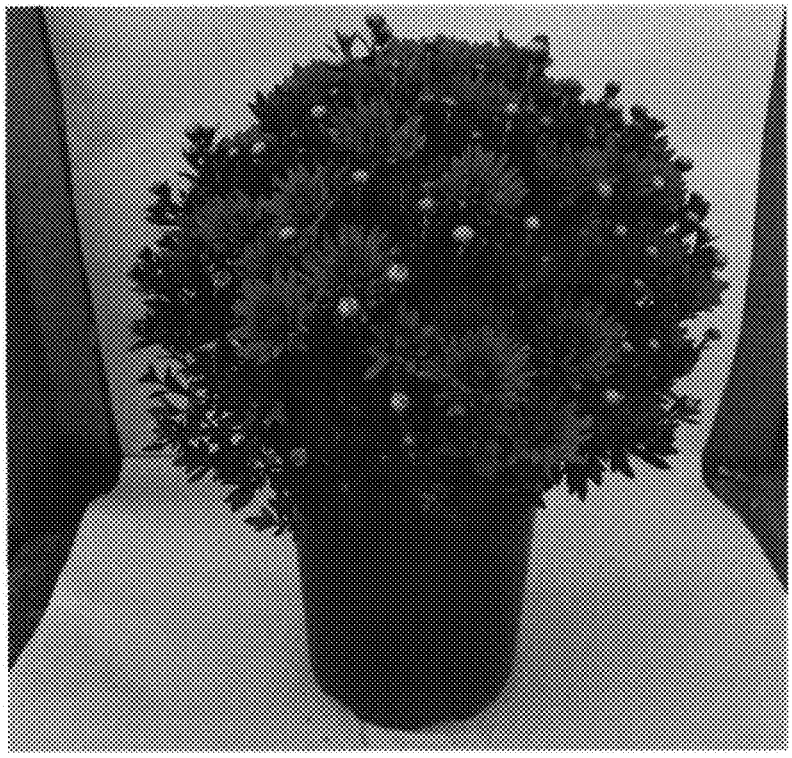

The aforementioned photographs: FIG. 1, as well as FIG. 2, were taken in August 2016 both showing a plant from the same natural outdoor trial in Gilroy, Calif. These plants were about 11 weeks of age. One rooted cutting per pot had been planted in a one gallon pot, not pinched in week 22. Plants started flowering in August.

DETAILED BOTANICAL DESCRIPTION

The measurements were taken in Gilroy, Calif. in August 2016 on the plants from the aforementioned trial.

Color references are made to The Royal Horticultural Society Colour Chart (R.H.S.) 2001.

TABLE 2

DIFFERENCES BETWEEN THE NEW VARIETY 'CIFZ0051' AND TWO MOST SIMILAR VARIETIES:

| | 'CIFZ0051' | 'Yocheryl', U.S. Plant Pat. No. 11,846 |
|---|---|---|
| Flowering response (blackcloth): | 2 days slower | 2 days faster |
| Flowering response (natural): | 1 week slower | 1 week faster |
| Flower color: | No two-tone effect in flower color | Has a two-tone effect in flower color |
| Flower size: | Smaller | Bigger |
| Plant habit or size: | Larger plant in blackcloth but smaller plant natural with fuller/rounder plant habit | Smaller plant in blackcloth but bigger plant natural with more open/more upright plant habit |

TABLE 3

| | | |
|---|---|---|
| Flowering response (blackcloth): | Similar | Similar |
| Flowering response (natural): | Similar except in the south where 'CIFZ0051' can be half a week slower than 'Amiko Violet' | Similar except in the south where 'Amiko Violet' can be a half a week faster than 'CIFZ0051' |
| Color fading: | Less fading | More fading |
| Flower color: | Darker lavender/pink color | Lighter lavender/pink color |
| Flower size: | Smaller | Bigger |
| Plant habit or size: | Similar | Similar |

Plant:

*Form, growth and habit.*—Herbaceous garden-type, stems upright and outwardly spreading, freely branching, strong and moderately vigorous growth habit.

*Plant height (above soil).*—20-22 cm.

*Plant height (inflorescence included).*—22-24 cm.

*Plant width.*—29-31 cm.

Roots:

*Number of days to initiate roots.*—About 4 days at about 22 degrees C.

*Number of days to produce a rooted cutting.*—14-16 days at 22 degrees C.

*Type.*—Fine, fibrous, free branching.

*Color.*—RHS N155B but whiter.

Foliage:

*Arrangement.*—Alternate.

*Immature leaf, color upper surface.*—RHS 137A.

*Immature leaf, color lower surface.*—RHS 137B.

*Mature leaf, color, upper surface.*—Between RHS 137B and RHS 137C.

*Mature leaf, color lower surface.*—RHS 137C.

*Length.*—2.3-2.5 cm.

*Width.*—1.9-2.9 cm.

*Shape.*—Ovate.

*Base shape.*—Attenuate.

*Apex shape.*—Acute.

*Margin.*—3 main lobes, irregularly serrated.

*Texture, upper surface.*—Bifid hairs.

*Texture, lower surface.*—Bifid hairs.

*Color of veins, upper surface.*—RHS 144B.

*Color of veins, lower surface.*—RHS 144B.

*Pattern of veining.*—Palmate.

*Petiole color.*—RHS 137B.

*Petiole length.*—1.1-1.5 cm.

*Diameter.*—0.15-0.2 cm.

*Texture.*—Covered with bifid hairs.

Stem:

*Quantity of main branches per plant.*—9-12.

*Color of stem.*—RHS 137A to RHS 137B.

*Length of stem.*—12-14 cm.

*Diameter.*—0.6-0.7 cm.

*Length of internodes.*—0.5-1.5 cm.

*Texture.*—Bifid hairs.

*Color of peduncle.*—RHS 137A.

*Length of peduncle.*—7-9 cm.

*Peduncle diameter.*—0.2 cm.

*Texture.*—Bifid hairs.

Inflorescence:

*Type.*—Compositae, solitary, decorative-type inflorescences borne terminally above foliage, ray florets arranged on a capitulum.

*Quantity of short days to flowering (response time).*—Approximately 6 weeks.

*Natural season flowering.*—Early-mid October.

*Quantity of inflorescences per plant.*—55-65, with many small buds developing.

*Lastingness of individual blooms on the plant.*—About six weeks from first color.

*Fragrance.*—Slightly spicy.

Bud (when showing color):

*Color.*—RHS 186A.

*Length.*—1.2-1.4 cm.

*Width.*—1.0-1.2 cm.

*Shape.*—Oblate.

Immature inflorescence:

*Diameter.*—3.2-3.4 cm.

*Color of ray florets, upper surface.*—RHS 78A.

*Color of ray florets, lower surface.*—RHS 78C.

Mature inflorescence:

*Diameter.*—4.0-4.2 cm.

*Depth.*—1.0-1.5 cm.

*Total diameter of disc.*—Very small; not visible as covered by the many rays.

*Receptacle color.*—RHS 145B.

*Receptacle height.*—0.6 cm.

*Receptacle diameter.*—0.4 cm.

Ray florets:

*Average quantity of florets.*—Between 80 and 110 in several whorls.

*Color of florets, upper surface (abaxial).*—RHS 87A.

*Color inner surface (adaxial).*—RHS 80A.

*Length.*—1.9-2.1 cm.

*Width/diameter.*—0.5-03 cm.

*Shape.*—Oblong to elliptical.

*Apex shape.*—Most often emarginated or praemorse.

*Base shape.*—Cuneate.

*Margin.*—Entire.

*Texture, upper surface.*—Smooth.

*Lower surface.*—Smooth.

Disc florets: None present.

Phyllaries:

*Quantity.*—30-35.

*Color, upper surface.*—RHS 137A.

*Color, lower surface.*—RHS 137B.

*Length.*—0.7-0.8 cm.

*Width.*—0.1-0.15 cm.

*Shape.*—Lanceolate.

*Apex shape*.—Acute.
*Base*.—Fused.
*Margins*.—Entire, some with papery edges.
*Texture, upper surface*.—Glabrous.
*Texture, lower surface*.—Bifid hairs.

Reproductive organs:
*Pistil*.—One.
*Length*.—0.3-0.6 cm.
*Style color*.—RHS 1C.
*Style length*.—0.35-0.4 cm.
*Stigma color*.—RHS 7D.
*Stigma shape*.—Bi-parted.
*Ovary color*.—RHS 145C.
*Ovary length*.—0.15 cm.
*Ovary width*.—0.1 cm.

Androecium:
*Stamens*.—None, as they are usually present in disc florets only, which are not developed.
*Fertility/seed set*.—Has not been determined to date.
*Disease/pest resistance*.—Has not been determined to date.

What is claimed is:

1. A new and distinct variety of *Chrysanthemum* plant named 'CIFZ0051' substantially as illustrated and described herein.

* * * * *